United States Patent [19]
Wiggins

[11] Patent Number: 5,637,687
[45] Date of Patent: Jun. 10, 1997

[54] METHODS AND COMPOSITIONS FOR ISOLATING NUCLEIC ACIDS

[76] Inventor: James C. Wiggins, P.O. Box 74, Seabrook, Tex. 77586

[21] Appl. No.: 115,184

[22] Filed: Aug. 31, 1993

[51] Int. Cl.$^6$ .................................................. C07H 1/00
[52] U.S. Cl. ................. 536/25.4; 536/25.41; 536/25.42; 435/6; 435/270
[58] Field of Search ................... 536/25.4, 25.41, 536/25.42; 435/6, 270

[56] References Cited

U.S. PATENT DOCUMENTS

| | | | |
|---|---|---|---|
| 3,147,185 | 9/1964 | Charney | 536/23.7 |
| 3,389,133 | 6/1968 | Gutcho | 536/25.41 |
| 4,843,155 | 6/1989 | Chomcznski et al. | 536/25.4 |
| 4,900,677 | 2/1990 | Hewitt | 435/6 |
| 4,935,342 | 6/1990 | Seligson et al. | 536/25.42 |
| 5,234,809 | 8/1993 | Boom et al. | 536/25.4 |
| 5,346,994 | 9/1994 | Chomczynski | 536/25.4 |
| 5,393,672 | 2/1995 | Ness et al. | 436/94 |

OTHER PUBLICATIONS

Logemann, J., et al., "Improved Method for the Isolation of RNA from Plant Tissues," *Analytical Biochem.*, 163:16–20 (1987).

Chomczynski, P., "Solubilization in Formamide Protects RNA from Degradation," *Nucleic Acids Research*, 20:3791–3792 (May 1992).

"Ultraspec RNA—Isolation of RNA" —Biotecx Product Bulletin (Oct. 1992), pp. 1–2.

Product bulletin: Schleicher & Schuell –S&S ELUTIP© Minicolumns (Keene, NH, 9 pages).

*Primary Examiner*—James O. Wilson
*Attorney, Agent, or Firm*—Laura G. Barrow

[57] ABSTRACT

Compositions and methods for isolating nucleic acids from biological tissues and cells and for tissue/cell solubilization for other molecular biological uses, wherein the compositions comprise, in part, novel combinations of chaotropic agents and aromatic alcohols which act synergistically to effect better tissue/protein solubilization. The inventive compositions further include aprotic solvents for deactivation of ribonucleases and denaturization of proteins, as well as detergents for enhancing cell lysis and nucleoprotein dissociation. The inventive methods also comprise the use of a centrifuge, a solid-support matrix, and a microporous membrane for final isolation of the precipitated nucleic acids, resulting in high yield and purity of the precipitated nucleic acid.

39 Claims, No Drawings

METHODS AND COMPOSITIONS FOR ISOLATING NUCLEIC ACIDS

BACKGROUND OF INVENTION:

1. Field of Invention

This invention relates to novel compositions and methods for isolating and purifying assay-ready nucleic acids, particularly DNA, RNA, and enriching for mRNA from biological tissues and cells. The isolated and enriched mRNA is suitable, without further manipulation, for Northern blot and PCR (PCR=polymerase chain reaction). In particular, the present invention comprises the use of a combination of chaotropic agents, aprotic solvents, and aromatic alcohols which work synergistically to result in improved purification and yield of nucleic acids in a relatively short period of time as compared to conventional methods of nucleic acid isolation and purification. The inventive nucleic acid compositions are also excellent tissue solubilization and protein denaturing agents for general use in the recovery and analysis of radioactive substrates and vital stains (e.g. $^3$H tritiated lysine and trypan blue) as well in the preparation of samples for liquid scintillation counting. The inventive nucleic acid isolation methods are further particularly useful in isolating nucleic acids from plants, which are typically difficult to extract.

2. Description of Related Art

With the increase demand for RNA and DNA for use in various molecular biological studies, there has come a need for a more efficient, more rapid, and clinically useful method for isolating these nucleic acids from biological tissues and cells. Several methods and compositions have been published relating to the isolation and purification of nucleic acids from a wide array of biological samples, including plant and bacterial cells, insect cells, as well as mammalian tissue. Most of these methods, however, are timeconsuming, require expensive centrifugation equipment, and require multiple manipulative steps which tend to decrease recovery yields.

One of the earlier methods for isolating RNA from biological tissue and cell samples was reported by Cox (*Methods in Enzymology*, 129B: 120–129 (1968)) and is directed to the use of guanidinium thiocyanate and guanidinium chloride as protein denaturants. The Cox method involves the addition of 6M guanidinium thiocyanate to ribosomes. The RNA is then precipitated by adding ethanol to the solution, followed by centrifugation to recover the RNA. This procedure takes two days to complete and requires relatively large concentrations of guanidinium salts.

A popular method of RNA isolation is disclosed in Chirgwin, et al. (*Biochim.*, 18: 5294–5299 (1979)). In that procedure, tissue containing RNA is homogenized in a solution containing guanidinium thiocyanate, sodium citrate, and 2-mercaptoethanol. The homogenate is then centrifuged, and the supernatant is decanted and mixed with acetic acid to lower the pH to 5. The RNA is precipitated upon the addition of ethanol and is recovered in pellet form by centrifugation. A modification of this procedure involves separating the RNA from the homogenate by ultracentrifugation through a cesium chloride gradient. This method, however, requires expensive centrifugation equipment, skilled technicians, and up to two days to complete. Consequently, only a very limited number of samples can be processed simultaneously.

Feramisco, et al. (*Molecular Cloning*, 194–195, Cold Springs Harbor Laboratory, Cold Springs Harbor, N.Y.) reports another RNA isolation procedure wherein RNA-containing samples are homogenized in a solution of 4M guanidinium thiocyanate, 20% sodium lauryl sarcosinate (SIGMA), and 2-mercaptoethanol. Following homogenization, an equal volume of heated phenol (60° C.) and sodium acetate pH 5.2 are added to the homogenate. Next, an equal amount of chloroform is added, and the mixture is cooled and centrifuged. The aqueous phase is decanted and reextracted several times with a phenol/chloroform solution in order to maximize the yield. The procedure requires a skilled technician and takes four to five hours to complete.

The current state of the art procedure for RNA isolation is disclosed in U.S. Pat. No. 4,843,155 to Chomczynski. This procedure utilizes a single monophasic extraction reagent consisting essentially of 2–5M of a guanidinium salt or acid, 40–60% phenol, optionally 2-mercaptoethanol as an antioxidant, and a sufficient amount of sodium acetate buffer to maintain the reagent at pH 4. Chomczynski discloses that a high yield of high quality RNA can be obtained by this procedure in three hours. The procedure involves homogenizing biological samples in the reagent described above, and then adding 10% chloroform to the homogenate. The resulting suspension is next centrifuged to effect separation of the suspension into an aqueous phase, organic phase, and interphase. The RNA remains concentrated in the upper aqueous phase while DNA, proteins, and cellular debris remain in the lower organic phase and interphase. The aqueous phase is decanted, and an equal portion of absolute isopropanol is added to precipitate the RNA. The precipitated RNA is subsequently centrifuged at 12,000 g to form a pellet. The supernatant is then decanted, and the resulting pellet is washed with 70% ethanol, recentrifuged, and allowed to dry. This reference expressly states that a significantly lower degree of RNA isolation will result if the pH of the reagent is not maintained at pH 4, and the concentration of water-insoluble organic solvent used to effect phase separation is not maintained at about 10% v/v.

The Chomczynski RNA isolation procedure described above, however, has several disadvantages, including the co-isolation of polysaccharides, which have the same absorbance as RNA, thus leading to inaccurate and false quantitation of RNA, as discussed in Puissant, C. and Houdebine, L., "An Improvement of the Single-Step Method of RNA Isolation by Acid Guanidinium Thiocyanate/Phenol/Chloroform Extraction," *Biotechniques*, 8:148–149 (1991). Further, Puissant and Houdebine maintain that the procedure requires relatively high concentrations of guanidinium salts (i.e. 2–4M) and phenol (40–60%), which have been shown to interfere with subsequent oligo-dT-cellulose chromatographic polyadenylated mRNA purification, for example. Additionally, the high concentration of phenol is undesirable due to its high toxicity.

As for RNA, several methods and procedures for the isolation of DNA from biological tissue/cell samples have been published. One of the earlier methods of isolating DNA was reported by Jones (*Biochim. Biophys. Acta*, 10: 607–612) and involves the use of alkyltrimethylammonium bromides to precipitate DNA. This procedure, however, takes one to two days to complete.

One of the classic procedures for isolating high molecular weight DNA was reported by Marmur (*Journal of Molecular Biology*, 3:208–218 (1961)). The method includes up to fourteen steps which are tedious and require a certain level of expertise to perform. For example, the method includes total nucleic acid precipitation, dissolution of nucleic acids, deproteinization, reprecipitation, RNase treatment to destroy unwanted RNA, a second deproteinization, reprecipitation, dissolution of DNA, and washing steps. The process generally requires one to two days, and the best expected yield of DNA is not greater than 50%. Marmur reports that the method requires tailoring in order to obtain efficient isolation of DNA from a wide variety of microorganisms.

Another procedure for isolating DNA was also described by Marmur. The procedure has fewer steps but requires cesium chloride high speed centrifugation for up to three days.

Gross-Bellard et al., European J. Biochem., 36:32-38 (1973) is directed to a method for isolating DNA from mammalian cells. In this procedure, cells are lysed with the detergent sodium dodecyl sulfate (SDS) and Proteinase K and then deproteinized with phenol:chloroform extraction.

A procedure for isolating RNA and DNA is described in U.S. Pat. No. 4,935,352 to Seligson et al., and is directed to the isolation of both nucleic acids from biological samples using an anion exchange resin. The isolation procedure requires first adding an agent comprising sodium lauryl sulfate (SDS) and Proteinase K, in conjunction with a detergent, to lyse the cells.

Many current DNA isolation methods continue to utilize variations of the twenty-three-year old method of Marmur, which involves many tedious time and labor intensive manipulations involving the use of hazardous phenol solvents. Consequently, there is a need for a rapid, simple, efficient, and safe method of isolating high molecular weight DNA from biological tissues/cells.

SUMMARY OF THE INVENTION

The present invention is related to improved methods and compositions for isolating nucleic acids from biological tissues and cells, including abnormal cells such as tumor cells and cancerous cells. In particular, the present invention is directed to improved nucleic acid isolation methods comprising the use of a superior denaturing and tissue solubilizing composition which further includes a combination of chaotropic agents and aromatic alcohols, most preferably benzyl alcohol. These agents act synergistically to better dissociate the nucleic acids from proteins to effect better tissue/protein solubilization as well as aid in rapid phase separation during extraction. Further, the chaotropic agents are present in lower concentrations to allow for selective protein denaturation to the exclusion of the nucleic acids and to allow for the isolation of nucleic acids from biological tissues sensitive to high concentrations of guanidinium salts (e.g. plants).

The inventive isolating compositions also include buffers, water, and at least one aprotic solvent which inactivates nucleases and denatures proteins to effectively disrupt and solubilize the tissue/cell sample. Detergents are also present for enhanced cell lysis and nucleoprotein disassociation.

Phenolic compounds such as phenol, for example, are present in the inventive nucleic acid isolating composition preferable for isolating RNA; however, their concentrations are significantly smaller compared to other nucleic acid isolation methods, thereby making the present isolation method less hazardous with which to work. In addition, the phenol, for example, in combination with the chaotropic agents and benzyl alcohol, for example, act synergistically to extract proteins. When the inventive isolating composition is used to isolate DNA, however, phenol is not required at all.

One notable advantage of the present inventive nucleic acid isolation composition is that the composition is particularly effective in isolating nucleic acids from plants, which are typically difficult to lyse due to their very rigid cell walls. Furthermore, the presence of smaller concentrations of chaotropic agents, particularly the guanidinium compounds, effect better isolation of nucleic acids, particularly RNA and DNA, from plants, which contain greater quantities of polysaccharides and tend to react with guanidinium compounds. When guanidinium compounds react with polysaccharides, globules are formed which are consequently very difficult to extract. In addition, residual guanidinium salts inhibit pellet dissolution. Thus, the lower concentration of guanidinium compounds tend to avoid these problems.

An alternate embodiment of the inventive nucleic acid isolating composition is preferred when isolating nucleic acids, particularly RNA, from cells cultured on solid supports, in particular plastic surfaces, and comprises dividing the composition into two separate reagents. In the most preferred embodiment, the first reagent (Reagent 1) comprises the chaotropic agents, detergents, and buffer while the second reagent (Reagent 2) comprises phenol, benzyl alcohol, aprotic solvents, buffer, and stabilizer. The cells are first lysed with Reagent 1, transferred to a separate tube, and then combined with Reagent 2. This alternate embodiment is advantageous in that lesser quantities of the inventive composition are required. Further, a higher quality RNA, in greater yield and purity, is obtained since the degradation by phenol of the polystyrene plates/flasks, wherein the dissolved plastics cause lysed cells to adhere to the plastic surface, is avoided.

The inventive nucleic acid isolation method comprises solubilizing the biological tissue or cells with the inventive nucleic acid composition described herein to form a solubilized sample. The sample is then extracted with a water-insoluble organic solvent to form a suspension. In the preferred embodiment, the suspension is capable of separating into an aqueous phase, an organic phase, and an interphase at unit gravity as well as by centrifugation. When the inventive method is used to isolate RNA, for example, the RNA is concentrated in the upper aqueous phase while DNA, polysaccharides, proteins, and other contaminants are concentrated in the lower organic phase and interphase. Conversely, when the inventive method is used to isolate DNA, the DNA is concentrated in the upper aqueous phase while the RNA and other contaminants are concentrated in the lower organic phase and interphase.

The nucleic acid is precipitated from the aqueous phase by preferably adding equal volumes of a lower alcohol solution comprising isopropanol or an isopropanol/salt solution, wherein the salt is LiCl or NaCl, for example. When isopropanol is used alone, the aqueous phase is centrifuged to yield a nucleic acid pellet precipitant which is subsequently washed at least once with ethanol, for example, and then dried. The total time required for isolation of nucleic acids by this "centrifuge-dependant" method is approximately 60 minutes.

Alternatively, when nucleic acid precipitation is accomplished by adding to the aqueous phase an isopropanol/salt solution, the aqueous phase is passed through a retaining means for retaining the nucleic acid, such as a solid-support matrix or a microporous membrane, for example, which is preferably housed in a column, such as a spin column or syringe push column, for example. Various solid-support matrices and columns typically used in the art may be employed, such as 37-74 micron polystyrene divinylbenzene (DVB) co-polymer beads (Kodak), for example. The nucleic acid adsorbs onto the matrix while polysaccharides, proteins, and other contaminants, including residual chaotropic agents and phenol which interfere with enzymatic activity and hybridization specificity, for example, are dissolved in the isopropanol/salt solution and elute through the matrix or column. The nucleic acid can then be eluted by washing the matrix with ultrapure water. The resulting nucleic acid has a high purity and is enzyme assay ready. Alternatively, the aqueous phase can be passed through a spin filter or push column comprising a microporous membrane that traps or retains the nucleic acid while allowing the other smaller contaminants to pass through.

The total time required for isolation and purification of nucleic acids by this "centrifugation-independent" method is approximately 30 minutes. Moreover, the inventive centrifuge-independent method is advantageous over centrifuge-dependant methods for nucleic acid isolation in that the yield of RNA is increased, primarily due to less RNA loss due to pellet manipulation, reprecipitation steps, heating of the pellet, and overdried pellets, all of which are common occurrence in other centrifuge-dependant nucleic acid isolation methods. The quality of the isolated nucleic acid is also increased using the inventive centrifuge-independent method due to the presence of fewer contaminants, almost all of which are effectively washed through the column. The quality of the isolated nucleic acid is also increased in that enzymes such as nucleases, for example, which cause degradation of the nucleic acids are also effectively washed through the column. Consequently, the inventive centrifuge-independent method for isolating nucleic acids is particularly advantageous for isolating nucleic acids from plants, which have high levels of polysaccharides, as well as mammalian liver, for example, which has a high glycogen content, since the polysaccharides and glycogen are more effectively eliminated by this method.

The inventive nucleic acid isolating compositions are particularly useful in solubilizing plant and bacterial cell walls which are typically very rigid and therefore hard to lyse. In addition, the present inventive compositions are advantageous in isolating nucleic acids from tumor cells which typically contain high levels of endogenous RNases, for example.

The present inventive nucleic acid isolation methods can further be adapted to "back extract" nucleic acids from the organic phase/interphase obtained from the present inventive nucleic acid isolation method as well as other nucleic acid isolation methods wherein a nucleic acid is present in an organic solvent or organic phase/interphase.

The present invention is further directed to the use of the inventive nucleic acid isolating compositions as effective tissue/cell solubilizing agents suitable for use in other applications, such as, for example, recovery and analysis of radioactive substrates and vital stains, including $^3$H tritiated lysine and trypan blue, for example. Trypan blue, for example, is used to qualitatively score for membrane permeability and cell viability. Thus, the ability to dissolve tissues and cells, and then quantitate the uptake of vital stains, should increase the use of these vital stains for such applications.

In addition, fluorescein isothiocyanate (FITC) and potentially other important immunological stains are soluble and stable in the present inventive nucleic acid isolating compositions so that the qualitative aspects of fluorescent tagging of cells and tissues can be quantitatively exploited upon dissolution. Additionally, the inventive nucleic acid isolating compositions are useful in the preparation of samples for liquid scintillation counting, offering toluene-free, and thus safer, formulations. The inventive composition further has potential utility in the development of kits to quantitate specific cell types labeled with specific second antibodies, for example.

DETAILED DESCRIPTION OF THE PREFERRED EMBODIMENTS:

I. Nucleic Acid Isolation:

a. Tissue/cell solubilization:

The present invention relates to a method for isolating nucleic acids from biological tissues and cells. In the preferred embodiment, the nucleic acids may be isolated from a variety of biological tissues and cells, including bacterial cells such as E. coli; various types of fungi; viruses; plant cells such as maize, geraniums, and pine needles insect tissue; mammalian tissues such as mouse tail and mouse liver, for example; and abnormal cells such as tumor cells and cancerous cells such as leukemia, for example. Nucleic acids can also be isolated from biological fluids such as blood, urine, and feces, for example.

The inventive method is particularly useful in extracting nucleic acids from plant cells, which typically have very rigid walls, thus making lysis difficult. In addition, isolation of nucleic acids from plants is further complicated by high levels of ribonuclease activity and complex cell wall components which are solubilized upon extraction. The present nucleic acid isolation method is effective in removing these impurities. Moreover, the inventive method is particularly useful in isolating nucleic acids, particularly RNA, from tumor cells, which typically have high levels of endogenous RNases which degrade the RNA.

The present invention comprises solubilizing the biological sample with a novel tissue/cell solubilization and denaturing composition to form a solubilized sample. The concentration of the inventive composition (w/w) present in the solubilized sample is preferably from about 5% to about 20%, more preferably 5% to 10%, and most preferably about 6.5%, depending upon the type of tissue or cell used. Thus, in the most preferred embodiment, about 5 to about 10×10$^6$ bacterial cells may be extracted per 1.0 ml of inventive composition, about 200 mg of plant tissue per 1.0 ml of inventive composition may be extracted, and about 50 to about 100 mg of mammalian tissue per 1.0 ml of inventive composition may be extracted, for example.

b. The Nucleic Acid Isolating Composition:

The term "inventive nucleic acid isolating composition" refers to the novel tissue/cell solubilizing and protein denaturing composition used in the isolation of nucleic acids, namely RNA and DNA, comprising at least one chaotropic agent, at least one aprotic solvent, an aromatic alcohol, water, a buffer, and at least one, and preferably two, detergents to aid in further cell lysis and nucleoprotein disassociation. For RNA isolation, the preferred nucleic isolating composition comprises at least two chaotropic agents, and further includes a phenolic compound, and preferably benzyl alcohol as the aromatic alcohol. When DNA is the desired nucleic acid, the inventive nucleic acid isolating composition does not require the presence of phenol. The absence of phenol is particularly advantageous due to its high toxicity. All of the components of the inventive nucleic acid isolating composition must be of molecular biology quality.

The chaotropic agents of the present invention function to alter the secondary and tertiary structures of proteins, polysaccharides, or nucleic acids. This activity can be achieved, for example, by causing the dissociation of proteins from the nucleic acid to cause unwinding. It has been discovered that this result can be better achieved by using at least two chaotropic agents which act synergistically.

In the present inventive nucleic acid composition, the chaotropic agents preferably comprise guanidinium compounds such as guanidinium thiocyanate and guanidinium chloride, for example; an alkali metal xanthogenate; an alkali metal iodide; urea; and trifluoracetate salts. The alkali metals that can be employed comprise Na, K, Li, and the like. In a preferred composition for isolating nucleic acids, wherein the desired nucleic acid is RNA, the chaotropic agents are potassium ethyl xanthogenate and a guanidinium compound, preferably guanidinium thiocyanate. In the most preferred composition for isolating RNA, three chaotropic agents are employed, preferably guanidinium thiocyanate, potassium ethyl xanthogenate, and sodium iodide. When DNA is the desired nucleic acid, a preferred composition comprises one chaotropic agent, preferably a guanidinium compound, and the most preferred embodiment for DNA isolation comprises two chaotropic agents, preferably a guanidinium compound and sodium iodide.

In a preferred embodiment for isolating RNA, the chaotropic agents preferably comprise, in combination, from about 15% to about 25% (w/w) of the composition. The inventive composition preferably comprises from about 10% to about 20% (w/w) of a guanidinium compound, more preferably 17% (w/w) and from about 0.10% to about 0.50% (w/w) potassium ethyl xanthogenate, more preferably from about 0.20% to about 0.30% (w/w), and most preferably about 0.24% (w/w). It should be noted that when a guanidinium compound is used, lower concentrations are especially conducive to the isolation of intact polyadenylated mRNA. Further, sodium iodide can be substituted for potassium ethyl xanthogenate in the same concentration ranges described above. In an alternate embodiment, urea may be substituted for the guanidinium compounds, wherein the urea preferably comprises from about 10% to about 40% (w/w) of the nucleic acid isolating composition.

In the most preferred embodiment for isolating RNA, the inventive nucleic acid isolating composition comprises three chaotropic agents, preferably comprising, in combination, from about 15% to about 19% (w/w %) of the composition. The three preferred chaotropic agents to be used in combination are guanidinium thiocyanate or guanidinium chloride, potassium ethyl xanthogenate, and sodium iodide. [The thiocyanate and chloride salts may be used interchangeably; however, for ease of explanation, reference will be made to guanidinium thiocyanate where applicable.] In this preferred embodiment of the inventive composition, guanidinium thiocyanate comprises from about 10 w/w % to about 20 w/w % of the composition, more preferably from about 15 w/w % to about 20 w/w %, and most preferably about 18 w/w %. Potassium ethyl xanthogenate comprises from about 0.10 w/w % to about 0.50 w/w % of the composition, more preferably from about 0.20 to about 0.30 w/w %, and most preferably about 0.24 w/w % of the composition. Finally, sodium iodide preferably comprises from about 0.50 w/w % to about 2.0 w/w % of the composition, most preferably about 1.0 w/w %.

In a preferred nucleic acid isolating composition, wherein the nucleic acid is DNA, the chaotropic agents employed comprise, in combination, from about 25 w/w % to about 55 w/w % of the composition. Further, a preferred composition for isolating DNA comprises from about 25 w/w % to about 50 w/w % of a guanidinium compound, more preferably from about 30 w/w % to about 40 w/w %, most preferably 40 w/w %, from about 0.001 w/w % to about 0.48 w/w % potassium ethyl xanthogenate, more preferably from about 0.01 w/w % to about 0.05%, and most preferably about 0.05 w/w %; and from about 0.5 to about 2.0 w/w %, most preferably about 1.0 w/w % of sodium iodide.

A more preferred composition for isolating DNA comprises one chaotropic agent, wherein the chaotropic agent is a guanidinium compound selected from the group consisting of guanidinium thiocyanate and guanidinium chloride, which preferably comprises from about 25 to about 50 w/w %, more preferably about 30 to about 40 w/w % and most preferably about 40 w/w % of the composition, depending upon the type of biological sample.

In the most preferred embodiment for isolating nucleic acids, wherein the desired nucleic acid is DNA, two chaotropic agents are employed, preferably comprising, in combination, from about 25 w/w % to about 55 w/w % of the composition. The two most preferred chaotropic agents to be used in combination are guanidinium thiocyanate and sodium iodide. In this embodiment of the inventive composition, guanidinium thiocyanate comprises from about 25 w/w % to about 50 w/w % of the composition, more preferably from about 35 w/w % to about 40 w/w %, and most preferably about 40 w/w % of the composition. Further, sodium iodide preferably comprises from about 0.50 w/w % to about 5.0 w/w % of the composition, more preferably from about 0.75 w/w % to about 1.0 w/w %, and most preferably about 1.0 w/w % of the composition.

Alternatively, urea and trifluoracetate salts may be used as suitable chaotropic agents in the present invention, either in lieu of or in combination with the other chaotropic agents. Preferably concentrations include from about 10 to about 40 w/w % of urea and from about 0.5 to about 2.0 w/w % of trifluoroacetate salts.

In addition to the chaotropic agents, the inventive nucleic acid isolating composition further comprises at least one aromatic alcohol, most preferably benzyl alcohol. Benzyl alcohol has unexpectedly been found to act synergistically with the chaotropic agents present in the composition to further enhance solubilization of the tissues/cell sample and dissociation of proteins from nucleic acids as well as work synergistically with phenolic compounds such as phenol, for example, to extract proteins. Benzyl alcohol is also the component that facilitates the unit gravity phase separation of the organic solvent/solubilized biological cell suspension. The preferred concentration of aromatic alcohols present in the inventive nucleic acid isolating composition for isolating RNA is from about 0.5 w/w % to about 10 w/w %, more preferably from about 1 w/w % to about 5 w/w %. For the isolation of DNA, the preferred concentration range of aromatic alcohols, preferably benzyl alcohol, is from about 30% to about 60% (w/w), more preferably from about 35% to about 40% (w/w)).

The aprotic solvents used in the present inventive nucleic acid isolating composition include at least one of the following solvents, for example: a formamide compound, preferably N,N-dimethylformamide (i.e. N,N-DMF), dimethylsulfoxide (i.e. DMSO), and sulfalone. Other examples of formamide compounds include N,N-diethylformamide. The most preferred aprotic solvent is N,N-DMF. The aprotic solvents of the inventive composition preferably comprise from about 1 w/w % to about 5 w/w %, most preferably about 5 w/w %, of the inventive composition where the desired nucleic acid is RNA. Where DNA is the desired nucleic acid, the aprotic solvents preferably comprise from about 0.01 w/w % to about 5 w/w %, more preferably about B w/w %, of the inventive composition.

Where the desired nucleic acid is RNA, the inventive nucleic acid isolation composition further includes a phenolic compound. The phenolic compounds of the present inventive composition include phenol and aglycan phenol, for example, which function to extract proteins to cause cell lysis as well as denature proteins. The preferred phenolic compound is phenol, which preferably comprises from about 20 w/w % to about 40 w/w %, more preferably from about 25 w/w % to about 35 w/w %, and most preferably about 35 w/w % of the composition.

When the inventive nucleic acid compositions include a phenolic compound such as phenol, for example, a stabilizing agent for stabilizing the phenolic compound is preferably included in the composition. Examples of suitable stabilizing agents include hypophosphorus acid and the buffer sodium citrate, more preferably hypophosphorus acid. In the most preferred embodiment of the present invention, the stabilizing agent comprises from about 0.01 to about 0.15 w/w % of the nucleic acid isolating composition.

The inventive nucleic acid isolating composition also contains at least one detergent or surfactant, preferably two, to aid in cell lysis and nucleoprotein disassociation. The most preferred detergents are sodium lauryl sarconsinate [SIGMA] and sodium 2-ethylhexyl sulfate [SIGMA] used in combination; although the use of only one of these two detergents is effective. The detergents present in the inventive composition comprise, in combination if more than one is used, from about 0.10 w/w % to about 0.80 w/w %, preferably from about 0.20 w/w % to about 0.30 w/w % of the composition. In the preferred composition, sodium 2-ethylhexyl sulfate preferably comprises from about 0.01 w/w % to about 0.40 w/w %, more preferably from about 0.01 w/w % to about 0.02 w/w % of the composition; and sodium lauryl sarconsinate comprises from about 0.10 w/w % to about 0.40 w/w %, more preferably from about 0.10 w/w % to about 0.20 w/w % of the composition.

For the isolation of RNA, the preferred embodiment of the inventive nucleic acid isolation composition further includes distilled RNase-free water, comprising preferably from about 45 w/w % to about 55 w/w %, more preferably about 48 w/w % of the composition. Where DNA is the desired nucleic acid, the preferred composition includes distilled nuclease-free water, preferably comprising from about 20 w/w % to about 30 w/w %, more preferably about 25 w/w % of the composition.

Finally, a sufficient amount of a buffer is added to maintain the composition at an acidic pH, preferably from about 4 to about 6, more preferably about 5, where the desired nucleic acid is RNA. Where DNA is the desired nucleic acid, a sufficient amount of a buffer is added to maintain the composition at a pH of from about 4 to about 10. The most preferred buffers include sodium acetate and sodium citrate. TRIS-HCl may also be used where the inventive nucleic acid isolating composition is used to isolate DNA. In the preferred embodiment of the nucleic acid isolating composition, sodium citrate is the most preferred buffer, comprising from about 5.0 w/w % to about 6.0 w/w %, more preferably about 5.5 w/w % of the inventive composition.

c. Alternate Two-Reagent Nucleic Acid Isolating Composition:

An alternate embodiment of the inventive nucleic acid isolating composition is preferred when isolating nucleic acids, particularly RNA, from cells cultured on plastic surfaces. This embodiment comprises dividing the composition into two separate reagents, and is thus referred to herein as the "inventive two-reagent nucleic acid isolating composition," where in the most preferred embodiment, the first reagent (Reagent 1) comprises the chaotropic agents, detergents, and buffer while the second reagent (Reagent 2) comprises phenol, benzyl alcohol, aprotic solvents, buffer, and stabilizing agent. The cells are first lysed with Reagent 1, transferred to a separate tube, and then combined with Reagent 2. Reagent 1 and Reagent 2 contain equal volumes.

The preferred chaotropic agents, aprotic solvents, detergents, buffers, and aromatic alcohols present in the present two-reagent composition are the same as those described thus far for the inventive nucleic acid isolating compositions. In a preferred embodiment of the present invention, the chaotropic agents present in Reagent 1 are potassium ethyl xanthogenate and a guanidinium compound, preferably guanidinium thiocyanate. In a preferred composition, three chaotropic agents are employed, preferably guanidinium thiocyanate, potassium ethyl xanthogenate, and sodium iodide. A preferred Reagent 1 comprises from about 20% to about 40% (w/w) of a guanidinium compound, more preferably about 38% (w/w), and from about 0.20% to about 1.00% (w/w) potassium ethyl xanthogenate, more preferably from about 0.40% to about 0.60% (w/w), and most preferably 0.48% (w/w). These chaotropic agents preferably comprise, in combination, from about 15% to about 25% (w/w) of Reagent 1.

In the most preferred embodiment, Reagent 1 preferably comprises from about 20 w/w % to about 40 w/w % of guanidinium thiocyanate, more preferably from about 30 w/w % to about 40 w/w %, and most preferably about 35 w/w %; from about 0.20 w/w % to about 1.00 w/w % of potassium ethyl xanthogenate, more preferably from about 0.40 to about 0.60 w/w %, and most preferably about 0.48 w/w %; and from about 1.0 w/w % to about 4.0 w/w % of sodium iodide, more preferably about 2.0 w/w %.

Reagent 1 may also include urea and trifluoracetae as suitable chaotropic agents, either in lieu of or in combination with the other chaotropic agents. Preferable concentrations include from about 10% to about 40% (w/w) of urea and from about 1.0% to about 4.0% (w/w) of trifluoroacetate salts.

Reagent 1 further comprises at least one detergent or surfactant, preferably two, to aid in cell lysis and nucleoprotein disassociation. The most preferred detergents are sodium lauryl sarconsinate [SIGMA] and sodium 2-ethylhexyl sulfate [SIGMA] used in combination; although the use of only one of these two detergents is effective. The detergents present in the inventive reagents preferably comprise, in combination if more than one is used, from about 0.20 w/w % to about 1.60 w/w %, and more preferably from about 0.40 w/w % to about 0.60 w/w % of the reagents. In the preferred reagents, sodium 2-ethylhexyl sulfate preferably comprises from about 0.02 w/w % to about 0.08 w/w %, more preferably from about 0.02 w/w % to about 0.04 w/w % of the reagents, and sodium lauryl sarconsinate comprises from about 0.20 w/w % to about 0.80 w/w %, more preferably from about 0.20 w/w % to about 0.40 w/w % of the reagents.

A sufficient amount of a buffer is contained in Reagent 1 and Reagent 2 to maintain the reagents at an acidic pH, preferably from about 4 to 6, more preferably about 5. The most preferred buffers include sodium acetate and sodium citrate. In the most preferred embodiment, sodium citrate is the most preferred buffer, comprising from about 10 w/w % to about 12 w/w % of Reagent 1 and Reagent 2.

Suitable aprotic solvents contained in Reagent 2 include at least one of the following solvents: a formamide compound, preferably N,N-DMF, DMSO, and sulfalone. Other examples of formamide compounds include N,N- diethylformamide. The most preferred aprotic solvent is N,N-dimethylformamide (i.e. N,N-DMF). The aprotic solvents preferably comprise from about 2 w/w % to about 10 w/w %, most preferably about 10 w/w % of the reagent.

The phenol present in Reagent 2 preferably comprises from about 40 w/w % to about 80 w/w %, of the reagent, more preferably from about 50 w/w % to about 70 w/w %, and most preferably about 70 w/w %. Further, the benzyl alcohol comprises from about 1.0 w/w % to about 20 w/w %, preferably from about 2 w/w % to about 10 w/w % and most preferably 5 w/w %. Reagent 2 further includes the same types and concentrations of buffers as in Reagent 1. Reagent 2 preferably contains a stabilizing agent such as sodium citrate and hypphosphorous acid, for example, more preferably hypophosphorus acid. In the most preferred embodiment, the stabilizing agent comprises from about 0.01 to about 0.15 w/w % of Reagent 2.

Finally, both reagents contain distilled RNase-free water, comprising preferably from about 45 w/w % to about 55 w/w %, more preferably about 48 w/w % of the reagents.

d. Centrifuge-Dependant Nucleic Acid Isolation Method:

After the biological sample is solubilized, using either the inventive nucleic acid isolating composition or the inventive two-reagent nucleic acid isolating composition, the resulting solubilized sample is extracted with a water-insoluble organic solvent to form a suspension, wherein the organic solvent preferably comprises from about 10% to about 30 (v/v) % of the resulting suspension, more preferably from about 15% to about 25% (v/v). Examples of the preferable water-insoluble organic solvents include chloroform and carbon tetrachloride, and more preferably chloroform. The organic solvents must be at least ACS grade.

Upon addition of the organic solvent, the suspension is shaken vigorously for about 30 seconds and then stored at 4° C. for about 5 minutes. The suspension is then separated into phases comprising an upper aqueous phase, a lower organic phase, and an interphase, wherein a first nucleic acid is concentrated in the upper aqueous phase while a second nucleic acid and contaminants such as proteins and polysaccharides, for example, are concentrated in the lower organic phase and interphase. ["First nucleic acid" refers to the nucleic acid concentrated in the aqueous phase, and "second nucleic acid" refers to the nucleic acid concentrated in the organic phase/interphase.] This separation step may be accomplished by centrifuging the suspension for about 10 to 15 minutes at from about 2,000 g to about 12,000 g at 4° C. in an Eppendorf Centrifuge, for example. In the more preferred embodiment, the suspension is allowed to separate "at unit g," (i.e. by simple gravitational force) for about 5 to about 15 minutes at 4° C., thereby obviating the need for any expensive centrifugation equipment.

Upon phase separation of the suspension, the aqueous phase is removed and transferred to a fresh tube. The next step involves the precipitation and final isolation of the first nucleic acid. In one embodiment of the present invention, referred to herein as the "centrifuge-dependant nucleic acid isolation method," the first nucleic acid is precipitated by adding preferably an equal volume of a lower alcohol. Examples of suitable lower alcohols, all of which must be at least ACS grade, include isopropanol and ethanol. In this embodiment (i.e. to isolate RNA), isopropanol is most preferred, followed by ethanol. The resulting solution is then stored at 4° C. temperature for about 5 to 10 minutes, followed by centrifugation for about 15 minutes at 12,000 g and 4° C. Where the first nucleic acid is RNA, RNA forms a white to yellow pellet precipitant, whereas when DNA is the first nucleic acid, the pellet precipitant formed is white to yellow in color.

Next, the supernatant is decanted, and the first nucleic acid pellet precipitant is washed, preferably by vortexing, with from about 1.0 ml to about 3.0 ml of a second lower alcohol per 1.0 ml of original composition used in the solubilization of the biological sample. Preferably, about 3.0 ml of 75% ethanol is added per 1.0 ml of original inventive composition used. The first nucleic acid precipitant is then dried briefly under vacuum for about 10 minutes prior to dissolution in nuclease-free water for subsequent use in experimentation. The entire process can be completed in approximately 60 minutes.

e. Alternate Centrifuge-Independent Nucleic Isolation Method:

In an alternate embodiment of the present inventive nucleic acid isolation method, referred herein as the "centrifuge-independent nucleic acid isolation method," the first nucleic acid is precipitated by adding an equal volume of an alcohol/salt solution, wherein said alcohol is a lower alcohol, preferably isopropanol. Other examples of alcohols include ethanol; however, ethanol is preferred for isolating RNA or DNA if used at a ratio of about 2.5:1 (All solvents must be at least ACS grade). The alcohol preferably comprises from about 98 v/v % to about 99.8 v/v % of the alcohol/salt solution. The salt contained in the alcohol/salt solution is an alkali metal salt selected from the group consisting of LiCl, NaCl, KCl, and the like (ACS grade or better). Other halogens, such as bromide for example, are considered within the scope of the present invention, as well. A preferred salt is LiCl, preferably present in a concentration of from about 2.0M to about 5.0M, more preferably about 4M, of the alcohol/salt solution. The more preferred salt is NaCl, preferably present in a concentration of from about 0.50M to about 3.0M, more preferably about 2.0M, of the alcohol/salt solution.

After the addition of the alcohol/salt solution to the aqueous phase, the aqueous phase is passed through a retaining means for retaining the first nucleic acid, wherein the retaining means comprises a solid-support matrix preferably contained in a syringe push column or a spin column, for example. A preferred matrix is a coated glass or plastic polystyrene solid support matrix. Examples of suitable solid-support matrices are listed in Table 1. In a preferred embodiment, a 11–19 micron polystyrene 1% DVB, copolymer solid-support matrix (e.g. Bangs Lab.) housed in a syringe push column is used. The most preferred matrices comprise a polystyrene matrix coated with a calcium phosphate (i.e. $Ca_2PO_4$) coating or a hydroxyalpetite matrix. In this embodiment, the first nucleic acid, which is precipitated by the alcohol, adsorbs onto the matrix while the polysaccharides and other contaminants such as phenol, salts, pigments, proteins, and chaotropic agents, for example, are selectively solubilized by the alkyl metal salt, and thus are washed out through the matrix along with the salt. The flow rate is preferably about 1 drop per second. The combination of chaotropic agents present in the present inventive nucleic acid isolating composition facilitates the ability of the first nucleic acid precipitant to adsorb onto the matrix versus pure nucleic acid/alcohol solutions, wherein the nucleic acids are not adsorbed as well. The matrix is then dried briefly, after which ultrapure first nucleic acid, free of polysaccharides, is eluted with an appropriate amount of water to obtain the concentration required for subsequent experimental procedures.

The isolation of nucleic acids utilizing this centrifuge-independent nucleic acid isolating method can be completed in about 30 minutes. In addition to being faster and requiring no expensive centrifugation equipment, the yield of nucleic acids is equal to or greater than that resulting from the inventive centrifuge-dependant nucleic acid isolation method. Moreover, the purity of the isolated nucleic acid is significantly greater using the inventive centrifuge-independent method than when the nucleic acid is isolate using the centrifuge-dependant method. The greater yield may primarily be due to the absence of a pellet precipitant that can be lost due to numerous manipulations. Incomplete pellet dissolution, which is typical, may also result in a lower yield and purity.

Alternatively, the retaining means for retaining the first nucleic acid may comprise a microporous membrane, preferably housed in a spin or push column, wherein the first nucleic acid-containing aqueous phase is passed through a microporous membrane, most preferably formed of a 100,000 molecular weight cut-off polysulfone (i.e. cut-off refers to the ability of the membrane to exclude molecules greater than or equal to 100,000 MW). The flow rate is preferably 1 drop per second. In this alternate embodiment of the centrifuge-independent nucleic acid isolation method, all contaminants fall through the pores of the membrane while the nucleic acid is retained on the membrane due to its larger size.

In another embodiment of the present invention using the microporous membrane, the membrane is contained in a basket, to which the aqueous phase containing the precipitated nucleic acid is placed. The basket is spun at from about 1,000 to about 2,500 g to remove the contaminants. The basket is removed, and an appropriate solute, such as water or TRIS, EDTA buffer, for example is added to dissolve the desired nucleic acids. The basket is gentlely shaken by vortexing, and the purified nucleic acids are decanted.

f. Nucleic acid purity/yield:

The amount of protein contamination in the isolated nucleic acid is determined by ultraviolet (UV) spectrophotometry using a Beckman Spectrophotometer, for example. The procedure involves placing 50–100 l of the nucleic acid solution in a quartz cuvette and then adding a quantity of water sufficient to fill the cuvette (typically a 1 ml cuvette). The cuvette is then placed in the spectrophotometer where the UV light absorbance is measured at two wavelengths: 260 nm and 280 nm. To measure purity, the ratio of the absorbances is determined by dividing the absorbance at 260 nm by the absorbance at 280 nm (i.e. the $A_{260}/A_{280}$ ratio). Proteins exhibit maximum absorbance at 280 nm while nucleic acids exhibit maximum absorbance at 260 nm. Thus, the 260/280 ratio for pure nucleic acid is approximately 2. It is important to note that polysaccharides absorb at the same wavelength as nucleic acids and, if present, can lead to inaccurate quantitation of the nucleic acid. Experimental results using the inventive centrifuge-dependant nucleic acid isolation method show a 260/280 ratio of between 1.8–2.00, where the isolated nucleic acid is RNA. Where the isolated nucleic acid was DNA, experimental results showed a 260/280 ratio of about 1.75.

The UV 260 nm absorbance results obtained for the nucleic acids isolated via the inventive centrifuge-independent isolation method were not significantly different from the centrifuge-dependant method, thus indicating no significant loss of nucleic acid due to the matrix. On occasion, the centrifuge-independent method resulted in greater 260 nm absorbances, indicating better yield. RNA isolated by the centrifuge-independent method had 260/280 ratios of approximately 1.91.

Northern blots of nucleic acids isolated from the inventive centrifuge-dependant and centrifuge-independent isolation methods, however, were performed. The Northern blots were stained with ethidium bromide and destained in water. The Northern blot for RNA obtained by the centrifuged-independent isolation method showed sharp bands free of fuzziness that is usually associated with co-transferred RNA contaminants such as polysaccharides, while the RNA Northern blot for RNA isolated by the inventive centrifuged-dependant method did show some fuzziness. Thus, these results are further evidence that the inventive centrifuge-independent isolation method may be superior in terms of obtaining a purer RNA, partially due, perhaps, to the ability of the alkali metal salt (e.g. NaCl, LiCl) in the alcohol/salt solution to better solubilize interfering nucleic acid contaminants, such as polysaccharides, for example. Further, 260/280 ratios obtained for nucleic acids isolated by the inventive centrifuge-independent nucleic acids isolation method indicated improved purity compared to the centrifuge-dependant method, with ratios ranging from about 1.80 to 1.93, where the nucleic acid was RNA, and from about 1.67 to about 1.81, where the nucleic acid was DNA.

II. Back Extraction of Nucleic Acids:

An additional feature of the present inventive nucleic acid isolation methods described thus far is that each method can ultimately be used to isolate nucleic acids by "back extraction" of the resulting interphase/organic phase. That is, the interphase/organic phase obtained during the separation step of the inventive nucleic acid isolation method may be further extracted to isolate the second nucleic acid concentrated therein by combining the interphase/organic phase with the inventive nucleic acid isolating composition preferable for extracting the second nucleic acid. For example, when the second nucleic acid is DNA, the organic phase/interphase containing the DNA may be further extracted by combining it with the inventive nucleic acid isolating composition preferable for isolating DNA. Likewise, where the second nucleic acid is RNA, the organic phase/interphase may be combined with the inventive nucleic acid isolating composition preferable for extracting RNA. Alternatively, when RNA is concentrated in the interphase/organic phase, the RNA can be back-extracted using a saturated phenol solution, pH 4.5. For ease of explanation, the following back extraction methods for isolating nucleic acids are explained with reference to the present inventive nucleic acid isolating methods. However, the present inventive nucleic acid back extraction method, with perhaps minor variations, can be used to back extract nucleic acids from organic solvents or organic phases obtained from other nucleic acid isolating methods wherein the desired nucleic acid is concentrated in an organic phase/interphase due to previous extraction with a water-insoluble organic solvent, for example. Further, both the inventive centrifuge-dependant and centrifuge-independent methods described herein for final isolation of the nucleic acid may be employed in the present inventive back-extraction method.

In the preferred embodiment, the second nucleic acid-containing organic phase and interphase obtained from the separation step of the inventive nucleic acid isolation method is removed and placed in a separate tube. Next, the inventive nucleic acid isolating composition preferable for isolating the second nucleic acid and a water-insoluble organic solvent are added to the organic phase to form a suspension. The inventive nucleic acid isolating composition preferably comprises from about 60 v/v % to about 70 v/v % of the suspension, more preferably about 62 v/v %, while the water-insoluble organic solvent comprises from about 10 v/v % to about 30 v/v %, more preferably from about 15% to about 18 v/v % of the suspension. The components comprising the inventive nucleic acid isolating composition for back extraction, as well as their concentrations, are the same as those already described for the inventive nucleic acid isolating composition. Examples of the preferred water-insoluble organic solvents include carbon tetrachloride and chloroform, with chloroform being the more preferred.

Next, the tube is shaken, preferably by hand, and centrifuged at about 7,500 g, or more preferably at unit g, to effect phase separation. The aqueous phase, now containing the back extracted second nucleic acid, is decanted and transferred to a fresh tube. An equal volume of a lower alcohol, preferably isopropanol, is added to precipitate the second nucleic acid. Other examples of suitable lower alcohols include ethanol. The aqueous phase is then centrifuged at 12,000 g at 4° C. for about 10 minutes, and the resulting second nucleic acid precipitant is washed with a second alcohol, preferably 70% ethanol, at least once, and dried. The amount of second alcohol used is preferably about 1.0 to 2.0 ml per 1.0 ml of the original biological tissue/cell sample extracted.

In an alternative embodiment of the inventive nucleic acid back-extraction method, RNA may be back extracted by using a saturated phenol solution, pH 4.5, which is substituted for the inventive nucleic acid isolating composition preferable for isolating RNA. In this embodiment, the saturated phenol preferably comprises from about 40 w/w % to about 60 w/w %, more preferably from about 50 w/w % to about 60 w/w % of the suspension.

III. Tissue/cell solubilization and protein denaturation:

In addition to being used for the isolation of nucleic acids, the inventive nucleic acid isolating compositions may be used as general tissue/cell solubilization and protein denaturing compositions suitable for many other uses, including recovery and analysis of radioactive substrates and vital stains, such as $^3$H tritiated lysine and trypan blue, for example.

In addition, fluorescein isothiocyanate (FITC) and potentially other important immunological stains are soluble and stable in the present inventive nucleic acid isolating compositions so that the qualitative aspects of fluorescent tagging of cells and tissues can quantitatively be exploited upon dissolution. Additionally, the inventive nucleic acid isolating composition is useful in the preparation of samples for liquid scintillation counting.

The inventive tissue/cell solubilizing composition is suitable for solubilizing a variety of biological samples, including mammalian tissue, plant tissue, and bacterial cells, and viruses, to form a solubilized sample. Other types of samples include biological fluids such as blood, urine, and feces, for example, as well as abnormal biological cells such as tumor cells and cancerous cells such as leukemia, for example. The concentrations of the inventive tissue/cell solubilizing composition used to solubilize the biological samples are the same as those described for the inventive nucleic acid isolating compositions, namely about 5% to about 20 (w/w) %, depending upon the type of biological sample used. Thus, about 1 ml inventive composition per about 200 mg of plant tissue, 1 ml of inventive composition per from about 50 to about 100 mg of mammalian tissue, and 1 ml inventive composition per from about 5 to about $10 \times 10^6$ of bacterial cells are preferable concentrations.

The inventive tissue/cell solubilizing composition comprises the same chaotropic agents, aprotic solvents, detergents, and aromatic alcohol as for the inventive nucleic acid isolating composition. In a preferred embodiment, the inventive tissue/cell solubilizing composition preferably comprises at least one, and more preferably two, chaotropic agents.

The inventive solubilizing compositions may comprise the same components at the same concentrations as described herein for the inventive nucleic acid composition preferable for isolating RNA. However, the most preferred embodiment of the inventive solubilizing composition comprises the same components and at the same concentrations as described herein for the inventive nucleic acid composition preferable for isolating DNA.

In the most preferred embodiment of the inventive solubilizing composition, two chaotropic agents are employed, preferably comprising, in combination, from about 25 w/w % to about 55 w/w % of the composition. The two most preferred chaotropic agents to be used in combination are guanidinium thiocyanate and sodium iodide. In this embodiment of the inventive composition, guanidinium thiocyanate comprises from about 25 w/w % to about 50 w/w %, more preferably from about 35 w/w % to about 40 w/w %, and most preferably about 40 w/w % of the composition. Further, sodium iodide preferably comprises from about 0.50 w/w % to about 5.0 w/w % of the composition, more preferably from about 0.75 w/w % to about 2.0 w/w %, and most preferably about 1.0 w/w % of the composition.

In addition to the chaotropic agents, the inventive solubilizing composition further comprises at least one aromatic alcohol, more preferably benzyl alcohol. The preferred concentration of aromatic alcohols present in the inventive solubilizing composition is from about 30 w/w % to about 60 w/w %, more preferably from about 35 w/w % to about 40 w/w %.

The aprotic solvents used in the present inventive solubilizing composition include at least one of the following solvents, for example: a formamide compound, preferably N,N-DMF, DMSO, and sulfalone. Other examples of formamide compounds include N,N-diethylformamide. The most preferred aprotic solvent is N,N-DMF. The aprotic solvents preferably comprise from about 0.01 w/w % to about 5 w/w %, and more preferably about 5 w/w % of the inventive solubilizing composition.

The present inventive solubilizing composition also contains at least one detergent or surfactant, preferably two, to aid in cell lysis and nucleoprotein disassociation. The most preferred detergents are sodium lauryl sarconsinate [SIGMA] and sodium 2-ethylhexyl sulfate [SIGMA] used in combination; although the use of only one of these two detergents is effective. The detergents present in the inventive solubilizing composition preferably comprise, in combination if more than one is used, from about 0.10 w/w % to about 0.80 w/w %, more preferably from about 0.20 w/w % to about 0.30 w/w % of the composition. In the preferred composition, sodium 2-ethylhexyl sulfate preferably comprises from about 0.01 w/w % to about 0.40 w/w %, more preferably from about 0.01 w/w % to about 0.02 w/w % of the composition, and sodium lauryl sarconsinate comprises from about 0.10 w/w % to about 0.40 w/w %, more preferably from about 0.10 w/w % to about 0.20 w/w % of the composition.

A preferred embodiment of the inventive solubilizing composition further includes water, preferably comprising from about 20 w/w % to about 30 w/w %, more preferably about 25 w/w % of the composition.

Finally, a sufficient amount of a buffer is added to maintain the inventive composition at a pH of from about 4 to about 10. The most preferred buffers include sodium acetate and sodium citrate. TRIS-HCl may also be used. In the preferred embodiment of the inventive solubilizing composition, sodium citrate is the most preferred buffer, comprising from about 5.0 w/w % to about 6.0 w/w %, more preferably about 5.5 w/w % of the composition.

The following examples do not limit the scope of the invention, but are intended to illustrate aspects of the invention.

EXAMPLE 1

Inventive nucleic acid isolating composition for RNA isolation:
Formulation 1:

The following components were combined at room temperature for about 30 minutes: 17.7 gm guanidinium thiocyanate, 1.0 gm sodium iodide, 35.0 gm phenol, 5.0 gm benzyl alcohol, 2.5 gm N,N-DMF, 0.20 gm sodium lauryl sarconsinate, 0.02 gm sodium 2-ethylhexyl sulfate, 0.01 gm hypophosphorus acid, 5.4 ml sodium citrate buffer pH 5, and a quantity sufficient amount of ultrapure water to bring the preparation to 100 ml.

Formulation 2:

The following components were combined at room temperature for about 30 minutes: 17.7 gm guanidinium thiocyanate, 0.24 gm potassium ethyl xanthogenate, 35.0 gm phenol, 5.0 gm benzyl alcohol, 2.5 gm sulfalone, 0.20 gm sodium lauryl sarconsinate, 0.02 gm sodium 2-ethylhexyl sulfate, 0.01 gm hypophosphorus acid, 5.4 ml sodium citrate buffer pH 5, and a quantity sufficient amount of ultrapure water to bring the preparation to 100 ml.

Formulation 3:

The following components were combined at room temperature for about 30 minutes: 17.7 gm guanidinium thiocyanate, 1.125 gm sodium iodide, 0.24 gm potassium ethyl xanthogenate, 35.0 gm phenol, 5.0 gm benzyl alcohol, 2.5 gm N,N-DMF, 0.20 gm sodium lauryl sarconsinate, 0.02 gm sodium 2-ethylhexyl sulfate, 0.01 gm hypophosphorus acid, 5.4 ml sodium citrate buffer pH 5, and a quantity sufficient amount of ultrapure water to bring the preparation to 100 ml.

EXAMPLE 2

Inventive nucleic acid isolating composition for DNA:
Formulation 1:

The following components were combined at room temperature for about 30 minutes: 40.0 gm guanidinium thiocyanate, 1.0 gm sodium iodide, 40.0 gm benzyl alcohol, 1.0 gm N,N-DMF, 0.20 gm sodium lauryl sarconsinate, 0.02 gm sodium 2-ethylhexyl sulfate, 5.4 ml sodium citrate buffer pH 5, and a quantity sufficient amount of ultrapure water to bring the preparation to 100 ml.

Formulation 2:

The following components were combined at room temperature for about 30 minutes: 20.0 gm guanidinium thiocyanate, 40.0 gm benzyl alcohol, 1.0 gm N,N-DMF, 0.20 gm sodium lauryl sarconsinate, 0.02 gm sodium 2-ethylhexyl sulfate, 5.4 ml sodium citrate buffer pH 8, and a quantity sufficient amount of ultrapure water to bring the preparation to 100 ml.

EXAMPLE 3

Nucleic acid isolation method (RNA)—centrifuge dependant:

200 mg of mouse liver was solubilized, by homogenization, in 2 ml of the composition described in Example 1 (formulation 1). 0.2 ml of chloroform (ACS grade) was added to the solubilized liver and shaken for about 30 seconds. The resulting suspension was centrifuged at 2,000 g at 4° C. for 15 minutes to effect phase separation into an aqueous phase, an organic phase, and an interphase. The RNA was contained in the upper aqueous phase while the DNA and contaminants were contained in the lower organic phase.

The aqueous phase (approximately 1 ml) was transferred to a fresh tube using a pipette. An equal volume of isopropanol (i.e. 1 ml) was added to the aqueous phase, and the aqueous phase was stored at 4° C. for 5 to 10 minutes. The aqueous phase was then centrifuged for 15 minutes at 12,000 g and 4° C. to form a white to yellow RNA pellet precipitant. The supernatant was decanted, and the RNA precipitant was washed once with 3 ml of 75% ethanol (ACS grade), by vortexing, and subsequently centrifuged for 5 minutes at 12,000 g and 4° C.

The RNA precipitant was dried briefly under vacuum for 10 minutes. The RNA precipitant was then dissolved by vortexing in RNase-free water. The UV absorbance of the precipitant was measured at 260 nm and 280 nm, and the 260/280 ratio obtained was 1.70.

EXAMPLE 4

Nucleic acid isolation method (RNA)—centrifuge-independent:

200 mg of mouse liver was solubilized in 2 ml of the composition described in Example 1 (formulation 1), by homogenization. 0.2 ml of chloroform (ACS grade) was added to the solubilized liver and shaken for about 30 seconds. The resulting suspension was held at 4° C. for 15 minutes to effect phase separation, at unit g, into an aqueous phase, an organic phase, and an interphase. The RNA was contained in the upper aqueous phase while the DNA and contaminants were contained in the lower organic phase.

The aqueous phase (approximately 1 ml) was transferred to a fresh tube using a pipette. An equal volume of an isopropanol/salt solution comprising about 98 to 99% isopropanol and 4M LiCl was added to the aqueous phase to precipitate the RNA and dissolve the polysaccharides and other contaminants. The aqueous phase was then loaded onto a polystyrene matrix contained in a push column, wherein the matrix was 11–19 micron polystyrene 1% DVB co-polymer particles (Bangs Lab.). The flow rate was 1 drop per second. The RNA precipitant was adsorbed onto the matrix and then eluted with water. The UV260/280 ratio obtained for the RNA precipitant was 1.93. Examples of suitable matrices are outlined in 5 Table 1.

TABLE 1

| Examples of suitable types of solid-support matrices used in the inventive nucleic acid centrifuge-independent isolation methods | |
|---|---|
| Manufacturer | Type of matrix |
| Kodak | 37–74 micron polystyrene co-polymer divinylbenzene (DVB) particles |
| Degussa Corp. (Degalan) | Polymethyl methacrylate beads (DEGALAN LP) |
| Bangs Lab. | 11–19 micron polystyrene 1% DVB, copolymer particles |
| Bangs Lab. | 13–16 micron polystyrene <1% DVB copolymer particles |
| Bio-Rad | Bio-Gel HTP hydroxyalpetite, DNA |

TABLE 1-continued

Examples of suitable types of solid-support matrices used in the inventive nucleic acid centrifuge-independent isolation methods

| Manufacturer | Type of matrix |
| --- | --- |
| LIDA | Grade Polystyrene copolymer cartridge, push column (size = >74 microns) |
| Bangs Lab. | Glass particles (106–212 microns) |

EXAMPLE 5

RNA Isolation Using the Inventive Centrifuge-Independent Method:

200 mg of mouse liver was solubilized in 2 ml of the inventive nucleic acid composition described in Example 1 (Formulation 1). 0.2 ml of chloroform was added to the solubilized liver, and the resulting suspension was centrifuged at 2,000 g at 4° C. for 10 minutes to effect phase separation.

The aqueous phase was divided into two equal 400 µl aliquots. One 400 µl aliquot served as the control and was processed as per the centrifuge-dependant method described in Example 3. The second 400-µl aliquot was mixed with an equal portion of about a 99% ethanol/4M LiCl solution to precipitate the RNA, and then applied to a matrix comprising 50 mg 11–19 micron polystyrene, 1% divinyl benzene, co-polymer microparticles (Bangs Lab.) contained in a push column. The flow rate was 1 drop per second. The immobilized RNA precipitate was washed with 1 ml of 70% ethanol and allowed to dry for 10 minutes. The matrix was subsequently washed three times with 200- 1 portions of RNase-free water to elute the RNA precipitant.

The 260/280 UV ratios were obtained for each fraction and the control, and the results are shown in Table 2.

TABLE 2

UV 260/280 ratios for Fractions 1–5 obtained from inventive centrifuge-independent nucleic acid isolating method and control sample obtained from inventive centrifuge-dependant nucleic acid isolating method described in Example 5.

| * | 260 nm | 280 nm | 260/280 ratio | RNA yield (mcg)/ 100 mg bio. sample |
| --- | --- | --- | --- | --- |
| 1 | 1.770 | 1.650 | 1.07 | |
| 2 | 0.730 | 0.232 | 3.14 | |
| 3 | 0.839 | 0.438 | 1.91 | 637.6 mcg |
| 4 | 0.018 | 0.009 | 2.00 | |
| 5 | 0.006 | 0.002 | 3.00 | |
| C | 0.842 | 0.485 | 1.73 | 640 mcg |

*Fraction 1: RNA-containing aqueous phase flow-through obtained after pass through column, but prior to the 70% ethanol wash.
Fraction 2: RNA-containing aqueous phase flow through 70% ethanol wash obtained after ejection through column.
Fractions 3 . 5: RNA-containing eluant obtained from column after first, second, and third 200 µl washings of RNase-free water.
C = control sample obtained after dissolving resulting pellet precipitant in 200 µl of RNase-free water.

EXAMPLE 6

Nucleic acid isolation method (DNA)—centrifuge dependant:

130 m9 of mouse liver was solubilized in 2 ml of the composition described in Example 2 (formulation 2), with gentle shaking, to solubilize the liver. 0.2 ml of chloroform (ACS grade) was added to the solubilized liver and shaken for about 30 seconds. The resulting suspension was centrifuged at 2,000 g at 4° C. to effect phase separation into an aqueous phase, an organic phase, and an interphase. The DNA was contained in the upper aqueous phase while the RNA and contaminants were contained in the lower organic phase.

The aqueous phase (approximately 1 ml) was transferred to a fresh tube using a pipette. An equal volume of isopropanol (i.e. 1 ml) was added to the aqueous phase, and the aqueous phase was stored at room temperature for 5 to 10 minutes, followed by centrifugation for 15 minutes at 12,000 g and 4° C. to form a white to yellow DNA pellet precipitant. The supernatant was decanted, and the DNA precipitant was washed once with 3 ml of 75% ethanol, by vortexing, and subsequently centrifuged for 5 minutes at 12,000 g and 4° C.

The DNA precipitant was dried briefly under vacuum for 10 minutes. The DNA precipitant was then dissolved by vortexing in a buffer solution comprising TRIS buffer, NaCl, and EDTA, pH 7.4. UV absorbances of the precipitant were measured at 260 nm and 280 nm, and the 260/280 ratio obtained was 1.75.

EXAMPLE 7

Isolation of DNA using the inventive centrifuge-dependant nucleic acid isolation method:

20 mg of mouse tail was solubilized in 1 ml of the inventive nucleic acid isolation composition as described in Example 2 (formulation 2). 20 µl of chloroform was added to the solubilized sample, after which the resulting suspension was centrifuged at 15,000 g for 10 minutes to effect phase separation. The aqueous phase was removed, and an equal volume of isopropanol (about 400 µl) was added to the aqueous phase. The aqueous phase was then centrifuged at 15,000 g for 10 minutes. The resulting DNA pellet precipitant was then washed with 75% ethanol, dried, and dissolved in 100 µl of ribonuclease-free water.

The UV absorbances were measured at 260 nm and 280 nm, and were 0.038 and 0.020, respectively. The 260/280 ratio was 1.9, indicating excellent purity, and the yield of DNA per 20 mg of mouse tail was 29 µg (per the quantification procedure described in an article by Fritsch, E. F. and Sambrook, J. in *Molecular Cloning: A Laboratory Manual*, ed. Maniatis, T., Cold Springs Harbor Press, Cold Springs Harbor, N.Y. (1982)).

EXAMPLE 8

Back extraction of DNA from inventive nucleic acid composition for isolating RNA:

DNA was back extracted from the organic phase obtained upon isolation of RNA from 100 mg mouse liver using 1 ml of the inventive nucleic acid isolating composition preferable for isolating RNA per the procedure described in Example 3. The RNA-containing aqueous phase was removed, leaving the interphase/organic phase. To the interphase/organic phase containing DNA was added 800 µl of the inventive nucleic acid isolating composition preferable for isolating DNA (as described in Example 2, formulation 1) and 160 µl of chloroform were added to the interphase/organic phase mixture, and the resulting suspension was shaken vigorously for 30 seconds and placed on ice for 3 minutes. The suspension was then centrifuged at 2,000 g for 10 minutes at 4° C., resulting in an upper aqueous phase containing the DNA and a lower organic phase. The aqueous phase was removed, and the DNA precipitated with an equal volume of 100% isopropanol. The aqueous phase was then centrifuged at 12,000 g for 10 minutes at 4° C. The resulting supernatant was removed, and the DNA pellet precipitant was washed two times with 70% ethanol and dried.

EXAMPLE 9

Back extraction of DNA from commercial RNA extraction preparation:

100 mg of mouse liver was homogenized in 1 ml of another commercial guanidinium thiocyanate/phenol composition ($RNA_{zol}$ B) (the commercial embodiment of the invention described in U.S. Pat. No. 4,843,155 to Chomczynski). The homogenized liver sample was then extracted with 0.1 ml of chloroform, and the resulting suspension was shaken for about 30 seconds. Phase separation was effected by centrifugation at 12,000 g, and the organic phase/interphase was removed. 800 µl of the inventive nucleic acid composition preferable for isolating DNA (as described in Example 2, formulation 1) and 160 µl of chloroform were added to the interphase/organic phase mixture, and the resulting suspension was shaken vigorously for 30 seconds and placed on ice for 3 minutes. The suspension was then centrifuged at 2,000 g for 10 minutes at 4° C., resulting in an upper aqueous phase containing the DNA and a lower organic phase. The aqueous phase was removed, and the DNA was precipitated with an equal volume of 100% isopropanol. The aqueous phase was then centrifuged at 12,000 g for 10 minutes at 4° C. The resulting supernatant was removed, and the DNA pellet precipitant was washed once with 70% ethanol and dried.

The resulting DNA precipitant was dissolved in 200 l of $H_2O$, and the UV absorbances were measured at 260 nm and 280 nm. The resulting absorbance at 260 nm was 0.756, the yield was 574.4 µg (per 100 mg mouse liver), and the 260/280 ratio was 1.75.

EXAMPLE 10

Back extraction of DNA from commercial RNA preparation:

200 mg of rat liver was homogenized in 2.5 ml of $RNA_{zol}$ B. The aqueous phase was removed, and the organic phase/interphase was back extracted with 800 µl of the inventive nucleic acid isolating composition preferable for isolating DNA as described in Example 9. The remaining procedure for isolating DNA was performed per the procedure described in Example 9.

The UV absorbances were measured at 260 nm and 280 nm. The absorbance at 260 nm was 1.04, and the 260/280 ratio was 1.50. The yield was 790 g/80 mg of liver.

EXAMPLE 11

Back extraction of RNA from inventive nucleic acid composition for isolating DNA:

RNA was back extracted from the organic phase obtained upon extraction of DNA from 65 mg of mouse liver using 1 ml of the inventive nucleic isolating composition preferable for isolating DNA per the procedure described in Example 6. The DNA-containing aqueous phase was removed, leaving the interphase/organic phase, to which 800 µl of the inventive nucleic acid isolating composition preferable for isolating RNA (as described in Example 1, formulation 1) and 160 µl of chloroform were added to the interphase/organic phase mixture, and the resulting suspension was shaken vigorously for 30 seconds and placed on ice for 3 minutes. The suspension was then centrifuged at 2,000 g for 10 minutes at 4° C., resulting in an upper aqueous phase containing the RNA and a lower organic phase. The aqueous phase was removed, and the RNA precipitated with an equal volume of 100% isopropanol. The aqueous phase was then centrifuged at 12,000 g for 10 minutes at 4° C. The resulting supernatant was removed, and the RNA pellet precipitant was washed once with 70% ethanol and dried.

EXAMPLE 12

Back extraction of RNA using saturated phenol:

RNA was back extracted from the organic phase obtained upon extraction of DNA from 100 mg of mouse liver using 1 ml of the inventive nucleic acid isolating composition preferable for isolating DNA per the procedure described in Example 6. The DNA-containing aqueous phase was removed, leaving the interphase/organic phase, to which 800µl of saturated phenol pH 4.5 (ARMRESCO) and 160 µl of chloroform were added to the interphase/organic phase mixture, and the resulting suspension was shaken vigorously for 30 seconds and placed on ice for 3 minutes. The suspension was then centrifuged at 2,000 g for 10 minutes at 4° C., resulting in an upper aqueous phase containing the RNA and a lower organic phase. The aqueous phase was removed, and the RNA precipitated with an equal volume of 100% isopropanol. The aqueous phase was then centrifuged at 12,000 g for 10 minutes at 4° C. The resulting supernatant was removed, and the RNA pellet precipitant was washed once with 70% ethanol and dried.

EXAMPLE 13

Alternate inventive nucleic acid isolating composition for isolating RNA from cells on plastic surfaces:

Two RNA isolating reagents (100 ml each) were prepared as follows: Reagent 1 was prepared by combining, at room temperature, 17.7 gm guanidinium thiocyanate, 1.125 gm sodium iodide, 0.24 gm potassium ethyl xanthogenate, 0.20 gm sodium lauryl sarcosinate, 0.02 gm sodium 2-ethylhexyl sulfate, and 2.7 ml sodium citrate buffer pH 5. Reagent 2 was prepared by combining, at room temperature, 35.0 gm phenol, 5.0 gm benzyl alcohol, 2.5 gm N,N-DMF, 2.7 ml sodium citrate buffer pH 5, and 0.01 gm hypophosphorus acid. A sufficient amount of water was added to each reagent to bring the total volume to 100 ml.

Primary chick embryo brain cells (approximately $1\times10^7$ cells) were lysed with Reagent 1, transferred to a fresh tube, and then combined with an equal volume of Reagent 2. To the tube, 0.2 ml of chloroform was added, and the resulting suspension was centrifuged at 2,000 g at 4° C. for 10 minutes to effect phase separation. The aqueous phase was removed, to which an equal volume of 100% isopropanol as added. The aqueous phase was then centrifuged at 12,000 g for 10 minutes at 4° C. The resulting supernatant was removed, and the RNA pellet precipitant was washed once with 70% ethanol and dried.

EXAMPLE 14

Comparison of U.S. Pat. No. 4,843,155 ('155) to Chomczynski versus the inventive nucleic acid isolating compositions—RNA isolation:

100 mg of mouse spleen was solubilized by homogenization in 1 ml of a commercial embodiment of the '155 composition ($RNA_{zol}$ B - Cinna Scientific), and another 100 mg of mouse spleen was solubilized, by homogenization, in 1 ml of the inventive nucleic acid composition described in Example 1 (formulation 1). Both samples were extracted as per their respective protocols (for the inventive composition, the procedure described in Example 3 was followed).

The RNA obtained from the inventive method was of a higher quality than the RNA obtained from the '155 method, as evidenced by gel electrophoresis (1% Agarose 80 V gel, run for 1.5 hours), which showed a 28S:18S ratio of about 2:1.5 for the '155 method versus a ratio of about 2:1 for the inventive method upon visual inspection (i.e. the 28S band appeared twice as large as the 18S band for the inventive method, for example). These results were indicative of less degradation due to RNases resulting from the inventive method, since the 28S band was twice as large as the 18S band. The inventive method thus offered better protection of the RNA from RNases, even though the inventive composition contained less guanidinium thiocyanate. Further, there was no visible smearing between the 28S and 18S bands for the inventive method as compared to the '155 gel, which did show smearing (i.e. smearing was indicative of RNase degradation).

EXAMPLE 15

Comparison of inventive RNA isolation methods:

300 mg of mouse liver was solubilized by homogenization with 6 ml of the inventive nucleic acid isolation composition as described in Example 1 (formulation 2). The resulting homogenate was quickly aliquoted to five separate 1.5 ml microcentrifugation tubes (1 ml homogenate/tube).

Samples A–C were extracted by the inventive centrifuge-dependant method. 100 μl of chloroform was added to 1 ml of homogenate. Phase separation was accomplished as indicated per each sample. An equal volume of 100% isopropanol was added to the aqueous phase of each sample to precipitate the RNA.

Samples D–E were extracted by the inventive centrifuge-independent method. 100μl of chloroform was added to 1 ml of homogenate. Phase separation was accomplished by allowing the suspension to separate at unit g. An equal volume of 98% isopropanol/2M NaCl was added to the aqueous phase of each sample to precipitate the RNA.

Sample A was extracted, and the RNA was isolated per the inventive centrifuge-dependant method, wherein phase separation was effected by centrifugation at 12,000 g for 15 minutes at 4° C.

Sample B was extracted, and the RNA was isolated per the inventive centrifuge-dependant method as described above; however, upon extraction with chloroform, the resulting suspension was allowed to separate into phases at unit g for 15 minutes at 4° C.

Sample C was extracted, and the RNA was isolated per the inventive centrifuge-dependant method as described above, except phase separation was effected by low speed centrifugation (2,000 g) for 15 minutes at 4° C.

Sample D was extracted, and the RNA was isolated per the inventive centrifuge-independent method as described above, except a polystyrene 1% divinylbenzene (50 mg) solid-support matrix, distributed by LIDA, was used in a push column.

Sample E was extracted, and the RNA was isolated per the inventive centrifuge-independent method as described above, except a polystyrene 1% divinylbenzene (50 mg) solid-support matrix, manufactured by Kodak, was used in a push column.

The UV absorbance was taken for each resulting fraction at 260 nm and 280 nm to determine purity. The results are shown in Table 3.

TABLE 3

UV 260/280 ratios for different RNA isolating methods, including the inventive centrifuge-dependant and centrifuge-independent nucleic acid isolating methods for RNA.

| Tube | Abs. 260 nm | Abs. 280 nm | 260/280 ratio |
| --- | --- | --- | --- |
| A | 0.425 | 0.285 | 1.49 |
| B | 0.463 | 0.296 | 1.56 |
| C | 0.498 | 0.315 | 1.58 |
| D | 0.426 | 0.265 | 1.61 |
| E | 0.455 | 0.262 | 1.73 |

EXAMPLE 16

RNA isolation from plant leaves:

Geranium leaves were frozen in liquid nitrogen and pulverized to a fine powder using a mortar and pestle. 1 ml of the inventive nucleic acid isolating composition as described in Example 1 (formulation 2) was added to 200 mg of the pulverized leaf material. The isolation of RNA was carried out per the procedure described in Example 4.

From 200 mg of the leaf material, 0.13 mg of intact, high quality RNA was isolated.

EXAMPLE 17

Isolation of RNA from leukemia cells:

HL-60 leukemia cells ($5\times10^6$ cells) were homogenized in 1 ml of the inventive nucleic acid composition described in Example 1 (formulation 2). The RNA was isolated according to the procedure described in Example 5. From $5\times10^6$ cells, 75 μg of intact, high quality RNA was isolated.

EXAMPLE 18

Isolation of nucleic acids from fungus (toadstools): RNA Isolation:

600 mg of toadstool fungus was homogenized, using a Teflon-glass homogenizer, in 5 ml of the inventive nucleic acid isolating composition described in Example 1 (formulation 1). The RNA was isolated per the procedure described in Example 3. UV absorbances were measured at 260 nm and 280 nm, and the resulting 260/280 ratio obtained was 1.72.

DNA Isolation:

600 mg of toadstool fungus was homogenized, using a Teflon-glass homogenizer, in 5 ml of the inventive nucleic acid isolating composition described in Example 2 (formulation 1). The DNA was isolated per the procedure described in Example 5.

I claim:

1. A method for isolating DNA from biological tissues and cell samples, comprising the steps of:
   (A) solubilizing said biological sample with a sufficient amount of a single composition to denature and solubilize said sample to form a solubilized sample, said solubilized sample comprising RNA, DNA and contaminants, wherein said composition comprises (a) at least one chaotropic agent, (b) an aromatic alcohol, and (c) a buffer present in an amount sufficient to maintain said composition at an alkaline pH;
   (B) extracting said solubilized sample with a water-insoluble solvent for a time sufficient to form a suspension;

(C) separating said suspension into phases comprising an upper aqueous phase, a lower organic phase, and an interphase wherein said DNA is concentrated in said aqueous phase and said RNA and contaminants are concentrated in said organic phase and said interphase; and (D) precipitating said DNA from said aqueous phase and recovering said precipitated DNA.

2. The method of claim 1, wherein said pH of said composition is from about 8 to about 10.

3. The method of claim 1, wherein said biological sample is selected from the group consisting of yeast and bacteria.

4. The method of claim 1, wherein said aromatic alcohol is benzyl alcohol.

5. The method of claim 4, wherein said composition comprises from about 30 w/w % to about 60 w/w % of benzyl alcohol and from about 25 w/w % to about 50 w/w % of at least one chaotropic agent.

6. The method of claim 1, wherein said chaotropic agents include sodium iodide and at least one guanidinium compound selected from the group consisting of guanidinium thiocyanate and guanidinium chloride.

7. The method of claim 5, wherein said at least one chaotropic agent is a guanidinium compound.

8. The method of claim 6, wherein said composition comprises from about 25 w/w % to about 50 w/w % of guanidinium compound and from about 0.5 w/w % to about 5 w/w % of sodium iodide.

9. The method of claim 7, wherein said composition comprises from about 25 w/w % to about 50 w/w % of guanidinium compound.

10. In a method for isolating nucleic acids from biological tissues and cell samples comprising the steps of:

(A) solubilizing a biological sample with a sufficient amount of a composition to denature and solubilize said sample to form a solubilized sample, wherein said composition comprises at least one chaotropic agent;

(B) extracting said solubilized sample with a water-insoluble solvent for a time sufficient to form a suspension; and (C) separating said suspension into phases comprising an upper aqueous phase, a lower organic phase, and an interphase wherein said first nucleic acid is concentrated in said aqueous phase and said RNA is concentrated in said organic phase and said interphase; the improvement comprising the steps of:

(D) precipitating said first nucleic acid from said aqueous phase; and (E) recovering said precipitated first nucleic acid by eluting said aqueous phase through a retaining means for retaining said first nucleic acid precipitant.

11. The method of claim 10, wherein said retaining means is a solid support matrix, wherein said first nucleic acid precipitant is adsorbed onto said matrix, and wherein said method further comprises:

(E) eluting said first nucleic acid precipitant from said solid support matrix by washing said matrix with a sufficient amount of water required to obtain a desired concentration of substantially pure first nucleic acid.

12. The method of claim 11, wherein said precipitating step comprises adding to said aqueous phase an alcohol/salt solution to form said first nucleic acid precipitant and to solubilized polysaccharides and other contaminants, wherein said solution comprises a lower alcohol selected from the group consisting of ethanol and isopropanol and wherein said salt is selected from the group consisting of NaCl, LiCl, and KCl.

13. The method of claim 10, wherein said composition further includes benzyl alcohol.

14. The method of claim 13, wherein said first nucleic acid is DNA.

15. The method of claim 14, wherein said composition further includes a buffer present in an amount sufficient to maintain said composition at an alkaline pH.

16. The method of claim 10, wherein said chaotropic agents include sodium iodide and at least one guanidinium compound selected from the group consisting of guanidinium thiocyanate and guanidinium chloride.

17. The method of claim 10, wherein said chaotropic agent is a guanidinium compound.

18. The method of claim 16, wherein said composition comprises from about 25 w/w % to about 50 w/w % of guanidinium compound and from about 0.5 w/w % to about 5 w/w % of sodium iodide.

19. The method of claim 17, wherein said composition comprises from about 25 w/w % to about 50 w/w % of guanidinium compound.

20. The method of claim 11, wherein said matrix is formed of a polystyrene resin.

21. The method of claim 20, wherein said polystyrene resin comprises a calcium phosphate coating.

22. The method of claim 11, wherein said matrix is formed of hydroxyalpetite.

23. The method of claim 10, wherein said nucleic acid is RNA.

24. The method of claim 10, wherein said composition further includes benzyl alcohol.

25. The method of claim 24, wherein said benzyl alcohol comprises from about 0.50 w/w % to about 10 w/w % of said composition.

26. The method of claim 23, wherein said chaotropic agent is a guanidinium compound comprising from about 23 w/w % to about 20 w/w % of said composition.

27. The method of claim 7, further comprising the steps of:

(E) adding a second composition to said organic phase and said interphase to back extract said RNA, wherein said second composition comprises a chaotropic agent and an aromatic alcohol;

(F) extracting said organic phase and said interphase with a solvent for a time sufficient to form a second suspension;

(G) separating said said second suspension into phases comprising an upper aqueous phase, a lower organic phase, and an interphase, wherein said RNA is concentrated in said second suspension aqueous phase; and (H) precipitating said RNA from said said suspension aqueous phase and recovering said precipitated RNA.

28. The method of claim of 27, wherein said second composition aromatic alcohol is benzyl alcohol.

29. A method for isolating nucleic acids from cell samples attached to solid plastic supports, comprising the steps of:

(A) solubilizing a cell sample attached to a solid plastic support within a vessel with a sufficient amount of a first reagent to lyse said cells and form a solubilized cell sample, said sample comprising RNA and DNA, and wherein said first reagent comprises (a) at least one chaotropic agent;

(B) transferring said solubilized sample to a second vessel;

(C) adding to said second vessel containing said solubilized cell sample a second reagent, wherein said second reagent comprises (a) phenol and (b) benzyl alcohol;

(D) extracting said solubilized cell sample with a water-insoluble solvent for a time sufficient to form a suspension;

(E) separating said suspension into phases comprising an upper aqueous phase, a lower organic phase, and an interphase wherein said RNA is concentrated in said aqueous phase and said DNA is concentrated in said organic phase and said interphase; and (F) precipitating said RNA from said aqueous phase and recovering said precipitated RNA.

30. The method of claim 29, wherein said benzyl alcohol comprises from about 1 w/w % to about 20 w/w % of said second reagent.

31. The method of claim 29, wherein said phenol comprises from about 40 w/w % to about 80 w/w % of said second reagent.

32. The method of claim 31, wherein said chaotropic agents include at least one guanidinium compound, a metal ethyl xanothogenate, and a metal iodide.

33. The method of claim 32, wherein said first reagent comprises from about 20 w/w % to about 40 w/w % of at least one guanidinium compound, from about 0.2 w/w % to about 1 w/w % metal ethyl xanthogenate, and from about 1 w/w % to about 4 w/w % metal iodide.

34. The method of claim 33, wherein said precipitated RNA is recovered by eluting said aqueous phase through a retaining means for retaining said RNA precipitant.

35. A method for isolating nucleic acids from biological tissues and cell samples, comprising the steps of:

(A) solubilizing said biological sample with a sufficient amount of a composition to denature and solubilize said sample to form a solubilized sample, said solubilized sample comprising RNA, DNA, and contaminants, wherein said composition comprises at least one chaotropic agent;

(B) extracting said solubilized sample with a water-insoluble solvent for a time sufficient to form a suspension comprising an aqueous phase and organic phase, wherein said RNA is concentrated in said aqueous phase and said DNA and said contaminants are concentrated in said organic phase;

(C) separating said aqueous phase from said organic phase within said suspension;

(D) precipitating said RNA from said aqueous phase and recovering said precipitated RNA;

(E) adding a second composition to said organic phase to back extract said DNA, wherein said second composition comprises a chaotropic agent and an aromatic alcohol;

(F) extracting said organic phase with a solvent for a time sufficient to form a second suspension comprising an aqueous phase and an organic phase, wherein said DNA is concentrated in said second suspension aqueous phase and said contaminants are concentrated in said second suspension organic phase; and (H) precipitating said DNA from said second suspension aqueous phase and recovering said precipitated DNA.

36. The method of claim 35, wherein said precipitated RNA and precipitated DNA are removed by eluting said aqueous phases through a retaining means for retaining said precipitants.

37. In a method for isolating nucleic acids from biological tissues and cell samples comprising the step of isolating a nucleic acid from a biological sample to form a solution containing said nucleic acid; the improvement comprising the steps of precipitating said nucleic acid from said solution and recovering said precipitated nucleic acid from said solution by eluting said solution through a retaining means for retaining said nucleic acid precipitant.

38. The method of claim 37, wherein said retaining means is a solid support matrix, and wherein said method further comprises:

(D) eluting said nucleic acid precipitant from said solid support matrix by washing said matrix with a sufficient amount of water required to obtain a desired concentration of substantially pure nucleic acid.

39. The method of claim 38, wherein said precipitating step comprises adding to said aqueous phase an alcohol/salt solution to form said nucleic acid precipitant, said solution comprising a lower alcohol selected from the group consisting of ethanol and isopropanol, and wherein said salt is selected from the group consisting of NaCl, LiCl, and KCl.

* * * * *